US 8,206,387 B2

(12) United States Patent
Michelson (10) Patent No.: US 8,206,387 B2
(45) Date of Patent: *Jun. 26, 2012

(54) INTERBODY SPINAL IMPLANT INDUCTIVELY COUPLED TO AN EXTERNAL POWER SUPPLY

(76) Inventor: Gary Karlin Michelson, Venice, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 13/092,063

(22) Filed: Apr. 21, 2011

(65) Prior Publication Data

US 2011/0196501 A1 Aug. 11, 2011

Related U.S. Application Data

(63) Continuation of application No. 12/313,896, filed on Nov. 25, 2008, now Pat. No. 7,935,116, which is a continuation of application No. 10/631,309, filed on Jul. 31, 2003, now Pat. No. 7,455,672, which is a continuation of application No. 09/404,396, filed on Sep. 23, 1999, now Pat. No. 6,605,089, which is a continuation of application No. 08/250,177, filed on May 27, 1994, now Pat. No. 6,120,502.

(51) Int. Cl.
*A61B 17/56* (2006.01)
(52) U.S. Cl. ............... 606/53; 606/60; 606/246
(58) Field of Classification Search ............ 606/53, 606/246, 247, 60–61; 623/11, 16; 433/173, 433/174
See application file for complete search history.

(56) References Cited

U.S. PATENT DOCUMENTS

| 1,137,585 A | 4/1915 | Craig |
| 2,065,659 A | 12/1936 | Cullen |
| 2,181,746 A | 11/1939 | Siebrandt |
| 2,243,718 A | 5/1941 | Moreira |
| 2,372,622 A | 3/1945 | Fassio |
| 2,514,665 A | 7/1950 | Myller |
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |

(Continued)

FOREIGN PATENT DOCUMENTS

CA 1020233 11/1977

(Continued)

OTHER PUBLICATIONS

A Direct Current Electrical Bone Growth Stimulation for Spinal Fusion, Kane, W.J., Spine, vol. 13, No. 3, Mar. 1988.

(Continued)

*Primary Examiner* — Michael A. Brown
(74) *Attorney, Agent, or Firm* — Martin & Ferraro, LLP (57) ABSTRACT

An electrical bone growth promotion apparatus for the delivery of electrical current to an implant surgically implanted between adjacent bone masses to promote bone growth to areas adjacent to the implant is disclosed. The apparatus of the present invention comprises a self contained implant having a surgically implantable, renewable power supply and related control circuitry for delivering electrical current directly to the implant and thus directly to the area in which the promotion of bone growth is desired. The desired areas of bone growth promotion may be controlled by conducting negative charge only to the desired location of bone growth promotion.

34 Claims, 7 Drawing Sheets

U.S. PATENT DOCUMENTS

| | | | |
|---|---|---|---|
| 2,842,131 A | 7/1958 | Smith | |
| 3,128,768 A | 4/1964 | Giestauts | |
| 3,298,372 A | 1/1967 | Feinberg | |
| 3,426,364 A | 2/1969 | Lumb | |
| 3,435,526 A | 4/1969 | Brancato | |
| 3,486,505 A | 12/1969 | Morrison | |
| 3,604,487 A | 9/1971 | Gilbert | |
| 3,605,123 A | 9/1971 | Hahn | |
| 3,709,219 A | 1/1973 | Halloran | |
| 3,720,959 A | 3/1973 | Hahn | |
| 3,750,652 A | 8/1973 | Sherwin | |
| 3,783,880 A | 1/1974 | Kraus | |
| 3,820,534 A | 6/1974 | Kraus et al. | |
| 3,848,601 A | 11/1974 | Ma et al. | |
| 3,855,638 A | 12/1974 | Pilliar | |
| 3,867,728 A | 2/1975 | Stubstad et al. | |
| 3,867,950 A | 2/1975 | Fischell | |
| 3,875,595 A | 4/1975 | Froning | |
| 3,888,260 A | 6/1975 | Fischell | |
| 3,892,232 A | 7/1975 | Neufeld | |
| 3,905,047 A | 9/1975 | Long | |
| 3,915,151 A * | 10/1975 | Kraus | 600/13 |
| 3,918,440 A | 11/1975 | Kraus | |
| 3,942,535 A | 3/1976 | Schulman | |
| 3,948,262 A | 4/1976 | Zaffaroni | |
| 3,952,334 A | 4/1976 | Bokros et al. | |
| 3,964,473 A | 6/1976 | Wickham | |
| 3,987,499 A | 10/1976 | Scharbach et al. | |
| 4,016,651 A | 4/1977 | Kawahara et al. | |
| 4,027,392 A | 6/1977 | Sawyer et al. | |
| D245,259 S | 8/1977 | Shen | |
| 4,051,905 A | 10/1977 | Kleine | |
| 4,059,115 A | 11/1977 | Jumashev et al. | |
| 4,070,514 A | 1/1978 | Eatherly et al. | |
| 4,082,097 A | 4/1978 | Mann et al. | |
| 4,086,701 A | 5/1978 | Kawahara et al. | |
| 4,124,026 A | 11/1978 | Berner et al. | |
| 4,142,517 A | 3/1979 | Stavropoulos et al. | |
| 4,168,326 A | 9/1979 | Broemer et al. | |
| 4,175,555 A | 11/1979 | Herbert | |
| 4,177,524 A | 12/1979 | Grell et al. | |
| 4,181,457 A | 1/1980 | Holmes | |
| 4,195,367 A | 4/1980 | Kraus | |
| 4,197,850 A | 4/1980 | Schulman et al. | |
| 4,206,516 A | 6/1980 | Pilliar | |
| 4,222,128 A | 9/1980 | Tomonaga et al. | |
| D257,511 S | 11/1980 | Zahn | |
| 4,232,679 A | 11/1980 | Schulman | |
| 4,237,948 A | 12/1980 | Jones et al. | |
| 4,259,072 A | 3/1981 | Hirabayashi et al. | |
| 4,262,369 A | 4/1981 | Roux | |
| 4,271,832 A | 6/1981 | Evans et al. | |
| 4,289,123 A | 9/1981 | Dunn | |
| 4,293,962 A | 10/1981 | Fuson | |
| 4,309,777 A | 1/1982 | Patil | |
| 4,328,593 A | 5/1982 | Sutter et al. | |
| 4,333,469 A | 6/1982 | Jeffcoat et al. | |
| 4,341,206 A | 7/1982 | Perrett et al. | |
| 4,349,921 A | 9/1982 | Kuntz | |
| 4,356,572 A | 11/1982 | Guillemin et al. | |
| 4,359,318 A | 11/1982 | Gittleman | |
| 4,401,112 A | 8/1983 | Rezaian | |
| 4,405,319 A | 9/1983 | Cosentino | |
| 4,414,979 A | 11/1983 | Hirshorn et al. | |
| 4,423,721 A | 1/1984 | Otte et al. | |
| 4,439,152 A | 3/1984 | Small | |
| 4,450,834 A | 5/1984 | Fischer | |
| 4,484,570 A | 11/1984 | Sutter et al. | |
| 4,492,226 A | 1/1985 | Belykh et al. | |
| 4,501,269 A | 2/1985 | Bagby | |
| 4,507,115 A | 3/1985 | Kambara et al. | |
| RE31,865 E | 4/1985 | Roux | |
| 4,530,360 A | 7/1985 | Duarte | |
| 4,535,485 A | 8/1985 | Ashman et al. | |
| 4,542,539 A | 9/1985 | Rowe, Jr. et al. | |
| 4,545,374 A | 10/1985 | Jacobson | |
| 4,547,390 A | 10/1985 | Ashman et al. | |
| 4,549,547 A | 10/1985 | Brighton et al. | |
| 4,552,200 A | 11/1985 | Sinha et al. | |
| 4,553,273 A | 11/1985 | Wu | |
| 4,554,914 A | 11/1985 | Kapp et al. | |
| 4,570,623 A | 2/1986 | Ellison et al. | |
| 4,570,624 A | 2/1986 | Wu | |
| 4,599,086 A | 7/1986 | Doty | |
| 4,600,000 A | 7/1986 | Edwards | |
| 4,602,638 A * | 7/1986 | Adams | 607/52 |
| 4,604,995 A | 8/1986 | Stephens | |
| 4,608,052 A | 8/1986 | Van Kampen et al. | |
| 4,611,581 A | 9/1986 | Steffee | |
| 350,420 A | 10/1986 | Dillon | |
| 4,619,264 A * | 10/1986 | Singh | 607/52 |
| 4,628,921 A | 12/1986 | Rousso | |
| 4,634,720 A | 1/1987 | Dorman et al. | |
| 4,636,217 A | 1/1987 | Ogilvie et al. | |
| 4,636,526 A | 1/1987 | Dorman et al. | |
| 4,645,503 A | 2/1987 | Lin et al. | |
| 4,653,486 A | 3/1987 | Coker | |
| 4,655,777 A | 4/1987 | Dunn | |
| 4,661,536 A | 4/1987 | Dorman et al. | |
| 4,665,920 A * | 5/1987 | Campbell | 607/51 |
| 4,677,883 A | 7/1987 | Lee | |
| 4,677,972 A | 7/1987 | Tornier | |
| 4,693,721 A | 9/1987 | Ducheyne | |
| 4,696,290 A | 9/1987 | Steffee | |
| 4,698,375 A | 10/1987 | Dorman et al. | |
| 4,710,075 A | 12/1987 | Davison | |
| 4,713,004 A | 12/1987 | Linkow et al. | |
| 4,714,469 A | 12/1987 | Kenna | |
| 4,721,103 A | 1/1988 | Freedland | |
| 4,736,738 A | 4/1988 | Lipovsek et al. | |
| 4,743,256 A | 5/1988 | Brantigan | |
| 4,743,260 A | 5/1988 | Burton | |
| 4,759,766 A | 7/1988 | Buettner-Janz et al. | |
| 4,759,769 A | 7/1988 | Hedman et al. | |
| 4,769,881 A | 9/1988 | Pedigo et al. | |
| 4,781,591 A | 11/1988 | Allen | |
| 4,790,303 A | 12/1988 | Steffee | |
| 4,820,305 A | 4/1989 | Harms et al. | |
| 4,830,000 A | 5/1989 | Shutt | |
| 4,834,757 A | 5/1989 | Brantigan | |
| 4,848,327 A | 7/1989 | Perdue | |
| 4,851,008 A | 7/1989 | Johnson | |
| 4,863,477 A | 9/1989 | Monson | |
| 4,865,603 A | 9/1989 | Noiles | |
| 4,877,020 A | 10/1989 | Vich | |
| 4,878,915 A | 11/1989 | Brantigan | |
| 4,903,882 A | 2/1990 | Long | |
| 4,904,260 A | 2/1990 | Ray et al. | |
| 4,904,261 A | 2/1990 | Dove et al. | |
| 4,911,718 A | 3/1990 | Lee et al. | |
| 4,913,144 A | 4/1990 | Del Medico | |
| 4,936,848 A | 6/1990 | Bagby | |
| 4,943,291 A | 7/1990 | Tanguy | |
| 4,955,885 A | 9/1990 | Meyers | |
| 4,955,908 A | 9/1990 | Frey et al. | |
| 4,957,495 A | 9/1990 | Kluger | |
| 4,960,420 A | 10/1990 | Goble et al. | |
| 4,961,740 A | 10/1990 | Ray | |
| 4,968,316 A | 11/1990 | Hergenroeder | |
| 4,969,888 A | 11/1990 | Scholten et al. | |
| 4,987,904 A | 1/1991 | Wilson | |
| 5,015,247 A | 5/1991 | Michelson | |
| 5,015,255 A | 5/1991 | Kuslich | |
| 5,026,373 A | 6/1991 | Ray et al. | |
| 5,030,236 A | 7/1991 | Dean | |
| 5,055,104 A | 10/1991 | Ray | |
| 5,059,193 A | 10/1991 | Kuslich | |
| 5,071,437 A | 12/1991 | Steffee | |
| 5,084,050 A | 1/1992 | Draenert | |
| 5,102,414 A | 4/1992 | Kirsch | |
| 5,116,304 A | 5/1992 | Cadwell | |
| 5,122,130 A | 6/1992 | Keller | |
| 5,123,926 A | 6/1992 | Pisharodi | |
| 5,192,327 A | 3/1993 | Brantigan | |
| 5,258,031 A | 11/1993 | Salib et al. | |
| 5,263,953 A | 11/1993 | Bagby | |
| 5,279,292 A | 1/1994 | Baumann et al. | |

| | | |
|---|---|---|
| 5,292,252 A | 3/1994 | Nickerson et al. |
| 5,306,309 A | 4/1994 | Wagner et al. |
| 5,364,399 A | 11/1994 | Lowery et al. |
| 5,370,662 A | 12/1994 | Stone et al. |
| 5,383,935 A | 1/1995 | Shirkanzadeh |
| 5,393,036 A | 2/1995 | Sheridan |
| RE34,871 E | 3/1995 | McGuire et al. |
| 5,396,880 A | 3/1995 | Kagan et al. |
| 5,397,364 A | 3/1995 | Kozak et al. |
| 5,425,772 A | 6/1995 | Brantigan |
| 5,435,723 A | 7/1995 | O'Brien |
| 5,441,527 A | 8/1995 | Erickson et al. |
| 5,489,307 A | 2/1996 | Kuslich et al. |
| 5,489,308 A | 2/1996 | Kuslich et al. |
| 5,522,899 A | 6/1996 | Michelson |
| 5,571,109 A | 11/1996 | Bertagnoli |
| 5,571,189 A | 11/1996 | Kuslich |
| 5,628,317 A | 5/1997 | Starkebaum et al. |
| 5,807,397 A | 9/1998 | Barreras |
| 6,120,502 A | 9/2000 | Michelson |
| 6,605,089 B1 | 8/2003 | Michelson |
| 7,455,672 B2 | 11/2008 | Michelson |
| 7,935,116 B2 * | 5/2011 | Michelson ............ 606/60 |
| 2009/0088857 A1 | 4/2009 | Michelson |

FOREIGN PATENT DOCUMENTS

| | | |
|---|---|---|
| DE | 1961531 | 7/1970 |
| DE | 2446039 | 9/1974 |
| DE | 3101333 A1 | 12/1981 |
| DE | 3132520 A1 | 6/1982 |
| DE | 3505567 A1 | 6/1986 |
| DE | 4104359 A1 | 2/1991 |
| EP | 0 162 005 | 4/1985 |
| EP | 0 260 044 | 3/1988 |
| EP | 0 307 241 | 3/1989 |
| EP | 0 499 465 A1 | 8/1992 |
| EP | 0 599 419 A2 | 6/1994 |
| FR | 0 179 695 | 4/1986 |
| FR | 2581336 | 11/1986 |
| SE | 106101 | 7/1939 |
| WO | WO 84/01298 | 4/1984 |

OTHER PUBLICATIONS

EBI Medical Systems, The SpF-T Spinal Fusion Stimulator: An Efficacious Adjunct that Meets the Diverse Needs of Spine Patients, Aug. 1991.

EBI Medical. Systems, The Use of Direct Current for Electrically Induced Osteogenesis, The Positive Effect of an Electronegative Charge on Bone Growth, Feb. 1993.

* cited by examiner

INTERBODY SPINAL IMPLANT INDUCTIVELY COUPLED TO AN EXTERNAL POWER SUPPLY

RELATED APPLICATIONS

This application is a continuation of application Ser. No. 12/313,896, filed Nov. 25, 2008 now U.S. Pat. No. 7,935,116, which is a continuation of application Ser. No. 10/631,309, filed Jul. 31, 2003, now U.S. Pat. No. 7,455,672, which is a continuation of application Ser. No. 09/404,396, filed Sep. 23, 1999, now U.S. Pat. No. 6,605,089, which is a continuation of application Ser. No. 08/250,177, filed May 27, 1994, now U.S. Pat. No. 6,120,502, all of which are incorporated herein by reference.

BACKGROUND OF THE INVENTION

1. Field of the Invention

This invention relates to interbody bone fusion devices, and more particularly to an apparatus and method for the delivery of electrical current to a spinal fusion implant and to interbody fusion material for inducing bone growth and aiding in spinal arthrodesis.

2. Description of the Related Art

The spine may be fused along any of its various surfaces, or internally within the interspaces of the vertebrae. Various interbody fusion devices have been developed to promote interbody fusions of the spine, such as that of Michelson, U.S. Pat. No. 5,015,247, issued on May 14, 1991, Brantigan U.S. Pat. No. 4,743,256, issued on May 10, 1988, and others. Such devices have helped to achieve spinal fusion by providing structural support, presenting bone promoting substances to the fusion site, increasing the surface area available to participate in the fusion, and by being both self-stabilizing and stabilizing to a spinal segment.

During normal bone repair, the area around the fracture of the bone exhibits negative charge. The application of electrical current to negatively charge a site in which spinal fusion is desired simulates the boners own normal repair process and promotes osteogenesis. The application of electrical current to negatively charge a site in which osteogenesis is desired, creates an electrochemical reaction ($4e^- + O_2 + 2H_2O \rightarrow 4OH^-$) which lowers the oxygen tension (decreasing the $O_2$) to stimulate osteoblastic activity and promote bone formation. Further, the formation of the hydroxyl radical ($OH^-$) raises the local tissue pH which of itself is favorable to bone production and further promotes increases in the presence of alkaline phosphatase, a very potent stimulant of bone formation in its own right. Still further, there appears to be a direct effect of electrical current to present a negative charge at the cellular level so as to upset the resting electrical potential of the cell membrane with a resultant electrical perturbation within the cell, the net effect of which is promotional to the cellular activity of bone formation. Finally, the electromagnetic field generated by the passage of electrical current appears to be independent of that current (on the basis of magnetism alone) to be promotional of bone growth, though the mechanism remains unknown.

Conversely, the application of electrical current to positively charge an area of bone inhibits osteogenesis and thus inhibits bone formation. Therefore, the application of electrical current to deliver positive charge to an area of bone may be used to control the bone fusion process so that it does not occur in undesired areas such as within the spinal canal.

The bone fusion process is a race against time, for eventually, the body will give up its attempt to complete that process. Well-known within the field of surgery is the use of electrical current delivered internally, or applied externally relative to a patient's body to promote bone growth and thus promote the bone healing or fusion process. However in regard to the spine, none of the interbody fusion devices of the past incorporate the use of electric current to stimulate bone growth, to increase the rate of osteogenesis and the spinal fusion process.

To date the use of electric current to promote bone growth in the spinal fusion process has taken two forms. The first is the use of an internally implanted electrical pulse generator, with a cathode wire leading from the pulse generator being wrapped about a bone plug harvested from the patient's body which is then inserted into the intervertebral space. These devices however have been continually plagued with problems that include breakage of the lead wires from the generator to the fusion site and a second surgery to remove the generator implanted in the patient's body at a remote location to the fusion site after the service life of the battery has expired. The power supplies of these implantable generators have been ineffective due to their limited service life, which may be shorter than the time needed to attain solid fusion, and problematic due to the potential for tissue damage in the event of a leak. The latter concern prompts most physicians to perform a second surgical procedure to explant the generator and internal battery supply. The additional surgery to explant the device increases the risk of infection and danger to the patient, and results in unnecessary additional costs.

The second form in which electric current has been used in the past to stimulate spinal fusion required the wearing, external to the body of the patient, of an electromagnetic coil or coils. Unfortunately, neither of these methods when utilized in conjunction with the known methods of interbody arthrodesis has proven fully effective.

Therefore, a need exists for the means and method of improving upon and/or perfecting the conjoined use of an improved interbody fusion device other than bone alone, and the promotion of bone growth with electrical current.

SUMMARY OF THE INVENTION

The present invention is directed generally to an apparatus and method for the delivery of electrical current to a surgically implanted device in a location in which bone growth is desired. More specifically, the present invention discloses an electrical bone growth promotion (EBGP) spinal fusion implant positioned within the intervertebral space between two adjacent vertebrae of the spine to promote and induce bone growth in the spinal fusion process. The EBGP implant of the present invention comprises a power supply and related control circuitry for delivering electrical current directly to the housing of the EBGP implant which is surgically implanted within the intervertebral space between two adjacent vertebrae. The housing of the EBGP implant of the present invention is at least in part electrically conductive such that at least a portion thereof serves as an active cathode to deliver negative charge directly to the spinal fusion site and to any bone material contained within the EBGP implant and thus directly to the area in which the promotion of bone growth is most desired. As positive charges do not promote bone growth, but actually induce resorption of bone, the areas of bone growth promotion may be controlled either by conducting only negative charges to the location for bone growth promotion is desired or by conducting negative charges to the area in which bone growth promotion is desired and at the same time conducting positive charges to any area in which bone growth is to be inhibited. Thus, the housing or a portion thereof, serves as an active cathode for delivering negative charge or a combination active cathode and active anode for delivering negative charge and for delivering positive charge, respectively, to bone mass.

As an electrical bone growth promotion apparatus, the EBGP implant of the present invention is not limited in its use with any particular spinal fusion implant. Many different embodiments of the EBGP implant of the present invention are possible. For example, in a first embodiment of the EBGP implant, an implantable power supply and related control circuitry are completely contained within a hollow central chamber of the housing of the EBGP implant such that the EBGP implant is a self-contained unit positioned within the intervertebral space between two adjacent vertebrae of the spine and may deliver electrical charge directly to the fusion site to promote spinal arthrodesis. The power supply and control circuitry may be contained in an extending portion of a cap used to close one end of the hollow central chamber of the housing and thus may be inserted into the EBGP implant which itself may in the remainder be filled with bone.

The EBGP implant of the present invention is a self-contained unit which overcomes the problems described above associated with the prior art devices for delivering electrical current to promote bone fusion. The EBGP implant of the present invention conducts electrical current via its housing, or a portion thereof, to an area of bone adjacent to the EBGP implant in which the promotion of bone growth is desired. As no lead wires are present, the problem of breakage of such wires experienced by the devices of the past has been overcome. Further, as the power supply and related control circuitry are fully contained within the EBGP implant of the present invention there is no need to implant a power supply and/or said related control circuitry at a remote location from the EBGP implant. Further still, as the power supply and related control circuitry become entombed in the bone mass upon completion of the bone fusion process, no additional surgery is required to explant the power supply and/or control circuitry as was the case with the prior art. Thus, as no explantation is required, the possibility of infection to the patient and other risks inherent to all surgical procedures are eliminated, while also substantially reducing the costs of utilizing electric current to promote bone growth in the bone fusion process.

In a first variation of the first embodiment, the external housing of the EBGP implant, the threaded portion, or any part of the housing of the EBGP implant, may be utilized as an active cathode by coupling the cathode lead from the power supply and/or control circuitry contained within the EBGP implant to the housing or a portion thereof. For example, the housing may be a spinal fusion implant such as that described by Michelson in U.S. Pat. No. 5,015,247, issued on May 14, 1991, and could utilize its continuous external thread much like a wound coil with the threaded portions being separated from one another and from the remainder of the spinal implant by an electrically non-conductive ceramic material, and further that non-conductive material itself may also be osteoinductive.

In a second variation of the first embodiment, the housing of the EBGP implant further includes an opening through which bone growth from one vertebra to a second adjacent vertebra may occur, Coaxial with the opening is a coil that is coupled to the cathode lead of the power supply. The coil acts as an active cathode to deliver a negative charge and promote bone growth through the opening and coil. In a further modification of this variation the cathode continues as a coil about the housing of the EBGP.

In a second embodiment of the EBGP implant of the present invention, any of a number of already known or conventional surgically implantable power supply units and related control circuitry may be placed within the body of the patient at a location remote to the spine. A lead wire couples the power supply and/or control circuitry to the housing of the EBGP implant, such as a spinal fusion implant, situated within the intervertebral space between and in contact with two adjacent vertebrae. The EBGP implant which is at least in part not made of bone, and that part also being electrically conductive, is used to conduct electrical current to the interbody spinal fusion mass. In one variation of the second embodiment, the entire housing of the EBGP implant is electrically conductive and functions as an active cathode to deliver negative charge to the area of bone adjacent thereto. In a second variation of the second embodiment, the housing of the EBGP implant may be made of a combination of electrically conductive and non-conductive materials such that a first portion of the housing of the EBGP implant is an active cathode specifically utilized for the delivery of the negative electrical charge as discussed above for the first variation of the first embodiment and a second portion of the housing is an active anode specifically utilized to deliver positive charge to the area in which bone growth is not desired. The area of the anode may be minimized to reduce the area in which bone growth is inhibited or may be larger such that the anode is used to prevent bone formation over a substantial area.

In order to make efficient use of the power supply, rather than conducting electrical current to the entire housing of the EBGP implant of the present invention which would require a large power supply, electrical current may be conducted only to the threads of the housing or to a wire coil insulated from the remainder of the housing. In this manner less current is drained from the power supply without reducing the effectiveness of the electrical charge delivered to the site in which bone fusion is desired since the electrical field created about the coil or threads extends beyond the coil of the threads.

In a third embodiment of the EBGP implant of the present invention, a spinal fusion implant is preferably implanted surgically within the intervertebral space between two adjacent vertebrae and is wholly or partially ferromagnetic. The spinal fusion implant is hermetically sealed in a jacket composed of a non-ferromagnetic, biocompatible material which may or may not be electrically conductive. An electromagnetic field is produced by an electromagnetic coil or coils worn external to the patient's body. The spinal fusion implant may be inductively coupled to the electromagnetic fields generated and transmitted by the external coils, and thereby generate its own electromagnetic field and accompanying electrical currents. These internal fields and currents are localized within that segment of the spine in which the spinal fusion implant is located, and will induce bone growth and promote the spinal fusion process.

In a first variation of the third embodiment, the EBGP implant is wholly or partially powered by electrical currents induced within the EBGP implant by the externally-applied electromagnetic fields. Likewise, any battery source integrated into the EBGP implant may be recharged via such electromagnetic induction to renew the service life of the battery source and thus extend the period of time in which bone growth may be electrically promoted. The EBGP implant in this embodiment delivers electrical current and replenishes the power supply when inductively coupled to externally applied electromagnetic fields.

In another embodiment of the EBGP implant of the present invention, the power supply is surgically implanted within the body of the patient, but at a location remote to the spine such as a subcutaneous implantation, and is rechargeable in response to the application of external magnetic fields.

In still another embodiment of the EBGP implant of the present invention, the battery source is charged by an external power source by ferromagnetic induction and continues to deliver charges via that battery source even after the activity of the external coil ceases.

OBJECTS OF THE PRESENT INVENTION

It is an object of the present invention to provide an electrical bone growth promotion implant in which a power supply, related control circuitry, and delivery system are entirely self-contained within a spinal fusion implant, thus eliminating the need to violate other body tissues to situate the implant, thereby limiting the extent of surgery, the time for surgery, the blood loss, and the risk of infection;

It is another object of the present invention to provide an electrical bone growth promotion implant for delivering electrical current to promote bone growth in a biomechanically and biophysiologically optimal place so as to induce spinal fusion within the compressive weight bearing axis of the spine;

It is yet another object of the present invention to provide an electrical bone growth promotion implant that eliminates the need for lead wires, the breakage of which has historically been a major source of failure in regard to the use of electrostimulators in general;

It is a further object of the present invention to provide an electrical bone growth promotion implant in which with successful arthrodesis, the encapsulated power supply and/or related control circuitry becomes permanently entombed in the bone fusion mass thus eliminating the need to perform a second surgical procedure for its removal;

It is still a further object of the present invention to provide an electrical bone growth promotion implant in which an active cathode is fully contained within the bone fusion mass;

It is another object of the present invention to provide an electrical bone growth promotion implant in which the power supply and/or related control circuitry combined is an internal extension of either a spinal fusion implant itself or of an insertable cap of the spinal fusion implant;

It is a further object of the present invention to provide an electrical bone growth promotion implant which will receive externally applied electromagnetic fields and thereby generate electromagnetic fields and electric currents affecting the bone within and adjacent to the space between two adjacent vertebrae; and It is yet a further object of the present invention to provide an electrical bone growth promotion implant in which the power source for delivering electric current to the implant is wholly or partially supplied or recharged by externally applied electromagnetic fields.

These and other objects of the present invention will become apparent from a review of the accompanying drawings and the detailed description of the drawings.

BRIEF DESCRIPTION OF THE DRAWINGS

FIG. 16 is a cross sectional side elevational view of a seventh alternative embodiment of the electrical bone growth promotion implant of the present invention having an insulated cap at one end, a cathode lead from an external power supply connected to.

FIG. 17 is an end view of the seventh alternative embodiment of the electrical bone growth promotion implant along 17-17 of FIG. 16.

FIG. 18 is a front elevational view of an externally worn electromagnetic energy transmitter for transmitting an electromagnetic energy field to an implanted spinal fusion implant.

FIG. 19 is a cross sectional view taken along lines 19-19 of FIG. 18 illustrating the transmission of electromagnetic energy generated by the electromagnetic energy transmitter to a spinal fusion implant positioned within the patient's spine.

DETAILED DESCRIPTION OF THE DRAWINGS

Figure 1:
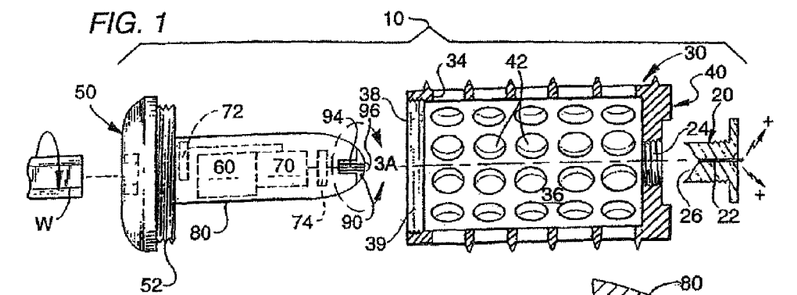
FIG. 1 is an exploded elevational side view, partially in cross section, of the electrical bone growth promotion implant of the present invention.
Figure 2:
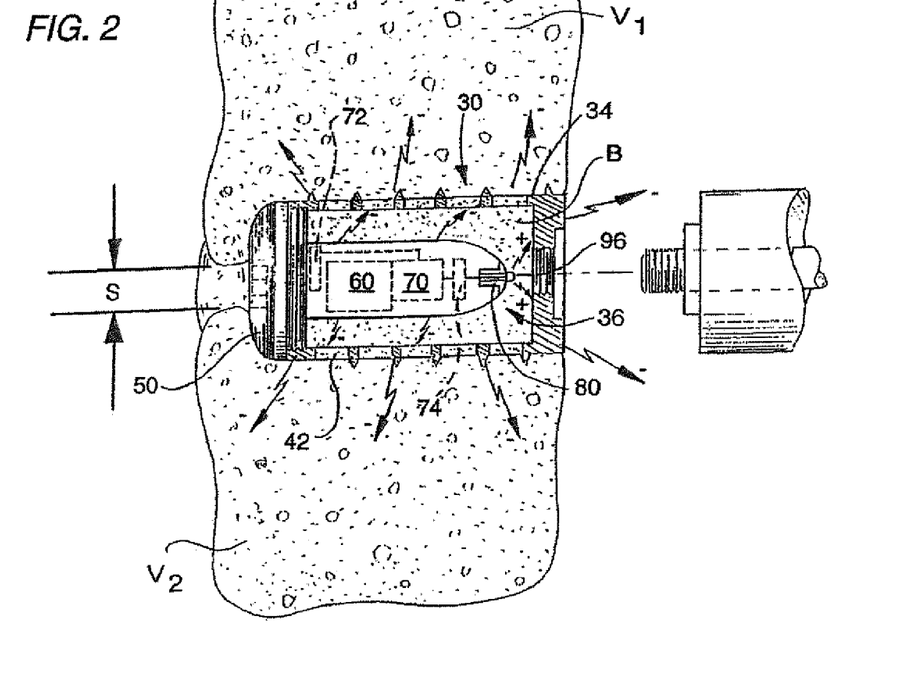
FIG. 2 is an elevational side view, partially in cross section, of the electrical bone growth promotion implant of the present invention inserted between two adjacent vertebrae of the spine.

Referring to FIGS. 1 and 2, the electrical bone growth promotion (EBGP) implant of the present invention is shown and is generally referred to by the numeral 10. In the preferred embodiment, the EBGP implant 10 comprises a housing 30 as shown in FIG. 2 which is implanted in the intervertebral disc space S between adjacent vertebrae $V_1$ and $V_2$ in a segment of the spine for achieving arthrodesis.

As shown in FIG. 1, housing 30 includes a hollow tubular body that is at least partially cylindrical having side walls 34 and preferably made of an surgically implantable and electrically conductive material such as, but not limited to, titanium. The housing 30 has a hollow central chamber 36 that is open at its distal end 38, is closed at its proximal end 40 and has a series of macro-sized openings 42 perforating the side walls 34. The macro-sized openings 42 preferably have a diameter in the range of approximately 2.0 mm to approximately 6.0 mm to allow for the macro fixation of the adjacent vertebrae $V_1$ and $V_2$. During the fusion process, bone growth occurs from each of the two adjacent vertebrae $V_1$ and $V_2$ through the macro-sized openings 42 to any natural or artificial bone fusion enhancing material that may be contained within the central chamber 36 so as to form a single solid mass.

The housing 30 has a similar structure and configuration of a spinal implant such as, but not limited to, the spinal fusion implant taught by Michelson in U.S. Pat. No. 5,015,247. The housing 30 is preferably, at least in part, electrically conductive and is made of material stronger than bone to provide structural support to the two adjacent vertebrae $V_1$ and $V_2$ while awaiting bone ingrowth, becoming firmly and permanently fixed in place once bone growth has occurred. To further enhance bone growth, the housing 30 may be coated with a bone growth inducing material such as, but not limited to, hydroxyapatite, hydroxyapatite tricalcium phosphate, bone morphogenic protein and the like. The housing 30 may also have a surface configuration that enhances bone growth such as, but not limited to surface knurling or roughening.

The open distal end 38 has internal threads 39 and is closeable with a cap 50 having at least a portion thereof that is electrically conductive. The cap 50 has a threaded end 52 which is threaded to match the internal threads 39 and secured to internal threads 39 by the use of a driver/wrench W or an equivalent tool.

Attached to and extending from the cap 50 is a casing 80 for containing electrical components discussed in greater detail below. The casing 80 is appropriately sized such that it fits within the central hollow chamber 36 of the housing 30 and occupies the least amount of space possible so as to limit interference with the bone fusion process. When the cap 50 is threadably coupled to the housing 30, the casing 80 is completely contained within the central hollow chamber 36 such that the EBGP implant 10 is a self-contained unit.

Referring to FIG. 2, the EBGP implant 10 is shown surgically implanted in the disc space S between the two adjacent vertebrae $V_1$ and $V_2$. At least a portion of the housing 30 is embedded into the bone of the adjacent vertebrae $V_1$ and $V_2$. However, it is appreciated that for the purpose of the present invention, the housing 30 need not be embedded into the bone of the vertebrae $V_1$ and $V_2$, but need only be placed adjacent to and be in contact with the vertebrae $V_1$ and $V_2$ in order to enable the EBGP implant 10 to conduct electrical current to the adjacent vertebrae $V_1$ and $V_2$.

It is to be understood that electrical current is a function of the time rate of change of electrical charge and the terms current and charge may be alternatively used depending upon context in describing the EBGP implants of the present invention. Further, as charge is proportional to the resistance encountered by the current, as bone growth occurs the resistance encountered by the current delivered to the bone mass will be increased, such that the charge will decrease. Also as the power supply depletes, the amount of current delivered over time will also decrease.

The hollow central chamber 36 can be filled with and may hold any natural or artificial osteoconductive, osteoinductive, osteogenic, or other fusion enhancing material. For example, bone material B harvested from the patient may be loaded into the central hollow chamber 36 as well as packed around the exterior of the housing 30, but within the intervertebral disc space S, wherein it is utilized in the spinal fusion process. An obdurator or similar instrument may be used to create a space in the bone material B for receiving an object therein such as the casing 80. In this manner, the housing 30 may be filled with bone material B and then closed with the cap 50 to hold the bone material B within the hollow chamber 36 during surgical implantation.

The casing 80 itself, or a portion thereof, is made of an electrically conductive and surgically implantable material such as, but not limited to, titanium such that electrical current applied to the casing 80 may be transferred from the casing 80 to the bone material B that is contained within the hollow central chamber 36. The casing 80 may be removably attached to the cap 50 or may be permanently affixed. In the preferred embodiment, the casing 80 is electrically coupled to the cap 50. However, it is appreciated that the casing 80 may be electrically insulated from the cap 50 if it is not desired to conduct an electrical current to the cap 50 or if it is desired to conduct an electrical current to the cap 50 having a different polarity from the remainder of the casing 80.

Within the casing 80 are the electrical components comprising a power supply 60, control circuitry 70, a cathode lead 72, and an anode lead 74. Both the power supply 60 and the control circuitry 70 are fully implantable and hermetically sealed. The cathode lead 72 is electrically coupled to the cap 50 either directly or via the casing 80, such that when the cap 50 is threaded to the housing 30, negative electrical charge is transferred to the housing 30 such that the housing 30 itself becomes an active cathode. In this manner, the power supply 60 is electrically coupled to the housing 30 and is located at the site in which spinal fusion is desired. Thus, in this embodiment, the EBGP implant 10 is a self-contained unit, thereby eliminating the need to implant the power supply 60 and related control circuitry 70 at a remote location within the patient's body, as is the case with fusion stimulators of the prior art.

The control circuitry 70 preferably includes well known means for the delivery of a constant current source, providing a single, preset current in the range of 0.01 to 20 uA. Thus, neither attachment of multiple cathodes or variation in cathodic area will alter the current density delivered to the bone fusion mass. It is appreciated that the control circuitry 70 may also include a wave form generator, a voltage generator or a clock means for delivering intermittent pulses of current with out departing from the scope of the present invention. Alternatively, the control circuitry 70 may comprise means for providing various patterns of direct current, alternating current, pulsatile current, sinusoidal current, or electrical noise generated by current rather than constant, direct current in order to promote bone growth. It is further appreciated that the electrical components may also comprise any of the well-known devices currently available to electrically stimulate spinal fusion, such as but not limited to the stimulator available from EBI Medical Systems, Parsippany, N.J., and may also be any of the devices suitable for delivering electric current and suitable for implantation well-known by those skilled in the art.

The control circuitry 70 is powered by the fully implantable, hermetically sealed power supply 60 which may be any of the well-known power supplies known in the art and currently commercially available and used to electrically promote spinal fusion such as, but not limited to, the power supply by EBI Medical Systems, Parsippany, N.J. The power supply 60 also may contain circuitry for generating electrical charge in response to externally applied electromagnetic fields.

Figure 3:
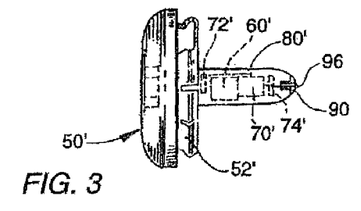
FIG. 3 is an alternative embodiment of the cap used for closing the open end of the electrical bone growth promotion implant of the present invention.

Referring to FIG. 3, alternatively, the power supply 60' may include battery recharge circuitry responsive to externally applied electromagnetic fields for recharging the battery. As a consequence, the overall size of the power supply 60' may be substantially reduced with a corresponding reduction in the size of the casing 80'. In this manner, any interference with the bone fusion process by the casing 80' is further reduced. Moreover, the longevity of the power supply 60' may be substantially increased as the power supply 60' may be recharged to extend its life beyond that of a conventional non-rechargeable battery having a fixed service life. As a result, the electric promotion of osteogenesis may be extended beyond the service life of conventional prior art devices with their non-rechargeable batteries. Further, the rechargeable power supply 60' may be reduced in size as the service life may be extended indefinitely, compactness of power supply such that bone growth promoting bone material is not displaced which is essential for fusion.

Also shown in FIG. 3, is an alternative embodiment of the cap 50' which may be secured to the housing 30 by a spring fastening means 52' which engages the interior surface of the housing 30 once the spring fastening means 52' is inserted in the central hollow chamber 36. In this embodiment, the time required to load bone material B within the central hollow chamber 36 and the time to assemble the cap 50' to the housing 30 is significantly reduced.

Figure 3A:
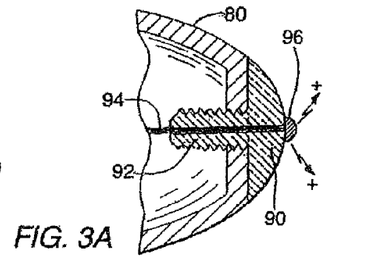
FIG. 3A is an enlarged fragmentary view along line 3A of FIG. 1 showing in cross section the end of the casing.

As shown in FIG. 3A, the end of the casing 80 includes an insulated screw 90 made of a non-conductive material. The screw 90 has a threaded portion 92 which threadably attaches to the casing 80, and has an electrically conductive core 94 passing through the longitudinal axis of the screw 90. The electrically conductive core 94 terminates at one end into an electrically conductive head portion 96 and is at its other end electrically coupled to the anode lead 74. In this manner, the head portion 96 becomes the active anode for delivering positive electrical charge to an area of bone. As previously noted positive electrical charge inhibits osteogenesis, the head portion 96 preferably has the smallest possible size to limit the area of contact to bone exposed to positive charge to limit bone resorption and is positioned at a location where the presence of positive charge will least interfere with the fusion process.

In the preferred embodiment, the head portion 96 is located at the tip of the end of the casing 80 such that when the cap 50 is attached to the housing 30, the head portion 96, and thus the active anode, is at a location which least interferes with the electrical promotion of the bone material B contained with the central chamber 36 and has substantially no contact with the adjacent vertebrae $V_1$ and $V_2$ to which fusion is desired. An example of the electrical current present in the EBGP implant 10 is illustrated by the electrical field arrows in FIG. 2.

As the promotion of bone growth occurs by the application of negative electrical current, the promotion of bone growth may be controlled by the application of negative electrical current only to the location in which bone growth is desired. For example, if bone growth promotion is desired at a particular location, negative current may be transferred to the housing 30 or a portion thereof which is adjacent to and in contact with a desired site in order to accelerate the fusion process. In areas where bone growth is not desired, such as near the canal of the spine for example, positive current may be transferred to the desired site.

Referring again to FIG. 1, in order to conduct positive charge from the head portion 96 (the active anode) the presence of which is undesired within the central hollow chamber 36, an insulated screw 20 having a conductive inner core 22 is threaded through an opening 24 in the proximal end 40. The insulated screw 20 has a recess 26 for receiving and coupling to the head portion 96. In this manner, positive charge is conducted by the conductive inner core 22 to a point external to the housing 30.

Figures 4, 5:
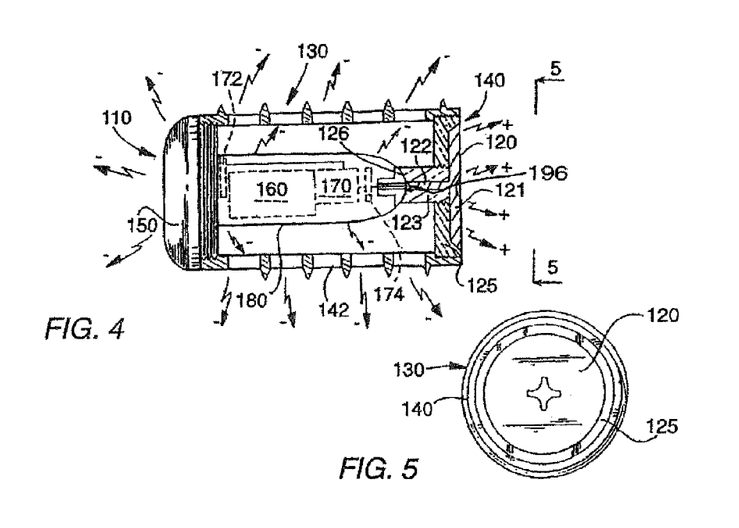
FIG. 4 is a side elevational view, partially in cross section, of a first alternative embodiment of the electrical bone growth promotion implant of the present invention having one end in which a portion thereof is made of a non-conductive material and insulated from the rest of the implant such that different polarities of electrical charges may be delivered to different parts of the implant as illustrated by the electrical field arrows.
FIG. 5 is an end view of the electrical bone growth promotion implant of the present invention along line 5-5 of FIG. 4.

Referring to FIGS. 4 and 5, a first alternative embodiment of the EBGP implant is shown and generally referred to by the numeral 110. The EBGP implant 110 comprises a housing 130 similar to the housing 30 described above, except that it has a proximal end 140 that is at least in part insulated from the remainder of the housing 130. The housing 130 has macro-sized openings 142 to permit bone growth therethrough. Anode lead 174 from the power supply 160 and/or control circuitry 170 may be electrically coupled to the proximal end 140 of the housing 130 so that the proximal end 140 may be positively charged. To accomplish this, the proximal end 140 has a screw 120 having a conductive screw head 121, a conductive inner core 122, and an insulated stem portion 123 having a recess 126 for coupling to the head portion 196 (the active anode.) The inner core 122 conducts positive charge from the head portion 196 to the conductive screw head 121. The screw head 121 is insulated from the housing 130 by an insulated ring 125 made of a non-electrically conductive material so that the screw head 121 can conduct positive charge to a point external to the housing 130 so that at least a portion of the proximal end 140 of the housing 130 becomes positively charged as illustrated by the electrical field arrows in FIG. 4. In this manner, the area of positive charge may be varied in size by varying the area of the screw head 121, and thus the area of potential promotion of bone resorption is also variable. As shown in FIG. 4, the area of screw head 121 has been deliberately increased to inhibit bone formation in an area adjacent to the screw head 121.

The configuration of electrical charges shown in the EBGP implant 110 would be utilized when the housing 130 is installed from the posterior aspect of the spine toward the anterior aspect of the spine since the proximal end 140 of the EBGP implant 110 would be proximate to the spinal canal once implanted in the disc space S between two adjacent vertebrae $V_1$ and $V_2$. By conducting positive charges to the proximal end 140 osteogenesis in the spinal canal which could compress the neural structures is inhibited.

It is appreciated that where negative electrical charge for the purpose of promoting bone growth is desired generally along the entire EBGP implant 110, then the positively charged screw 120 would have a screw head 121 proportionally much smaller in size to limit the area of positive electrical charge.

For the areas adjacent to the housing 130 in which bone growth and fusion is desired, the cathode lead 172 from the power supply 160 and/or control circuitry 170 is coupled to the casing 180 and negative charges are conducted to the housing 130 by the contact of the casing 180 and cap 150 with the housing 130 such that the housing 130 itself becomes an active cathode.

It is further appreciated that the delivering of positive charges and the negative charges may be reversed simply by interchanging the anode lead 174 and the cathode lead 172 coupling points to the housing 130, cap 150, distal end 140, or screw 120. In this way, negative charge may be applied and directed only to the particular areas in which bone growth is desired depending on the type of surgery, bone growth, and fusion desired.

Figure 6:
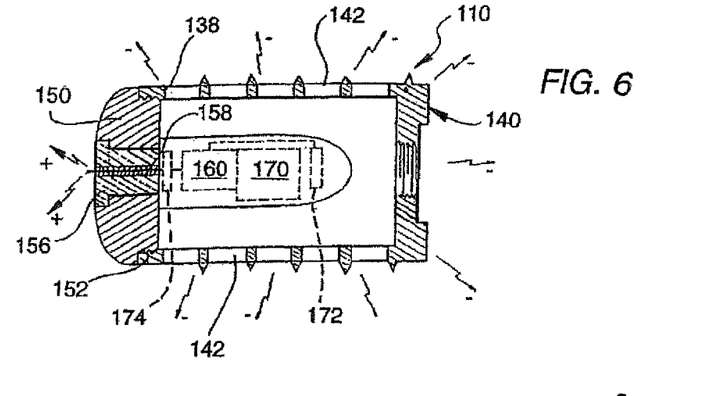
FIG. 6 is a cross sectional, side elevational view of a second alternative embodiment of the electrical bone growth promotion implant of the present invention having a cap at one end in which a portion thereof is made of non-electrically conductive material.

Referring to FIG. 6, for example, if the EBGP implant 110 is installed from the anterior aspect toward the posterior aspect of the spine, the distal end 138 of the housing 130 would be proximate to the spinal canal. In order to prevent undesired bone growth near the spinal canal, the distal end 138 of the housing 130 or a portion thereof, which when implanted is adjacent to and in contact with the bone near the housing 130, may be insulated from the remainder of the housing 130. Further, the distal end 138 may be positively charged by being connected to the anode lead 174 of the generator 160 so that the proximal end 138 itself serves as an active anode. This can be accomplished by having an insulated screw 156 having an electrically conductive core 158. The electrically conductive core 158 becomes the active anode and delivers positive electrical charge to the adjacent bone area. Thus, bone area adjacent to and in contact with the distal end 138 would be exposed only to positive charge and not to bone growth promoting negative charge. Further, in order to minimize bone resorption, the diameter of the electrically conductive core 158 may extend from the insulated screw 156 and may be decreased in size to limit the bone area being exposed to positive electrical charge.

The application of different polarity charges to different areas of the housing 130 may also be accomplished by having the threads 152 of a cap 150 coated with a non-conductive material such as, but not limited to, a ceramic material in order to insulate the cap 150 from the remainder of the housing 130 such that the cap 150 becomes the active anode when connected to the anode lead 174 and is positively charged. This will prevent electrical promotion of bone growth in the vicinity of the cap 150 which is adjacent to the spinal canal and in contact with the bone near the spinal canal when implanted. However, it is appreciated that other means of insulating the distal end 138 well-known by those skilled in the art, may be employed so that the distal end 138 has a different charge than the remainder of the housing 130 or has no charge at all.

Figures 7, 8A, 8B, 9:
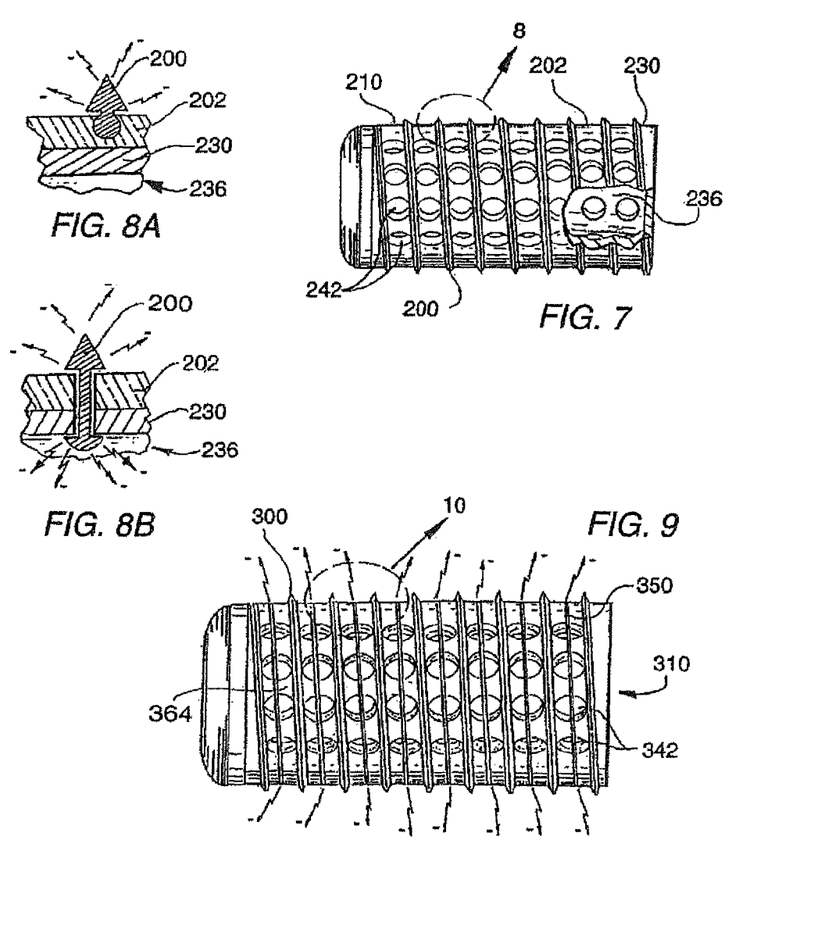
FIG. 7 is a side elevational view of a third alternative embodiment of the electrical bone growth promotion implant of the present invention having outer threaded portions that are separated from the rest of the implant by a non-electrically conductive insulating material.
FIG. 8A is an enlarged fragmentary cross sectional view of the third alternative embodiment of the electrical bone growth promotion implant taken along line 8 of FIG. 7 showing the threaded portion being anchored to the non-electrically conductive material.
FIG. 8B is an enlarged fragmentary cross sectional view of the third alternative embodiment of the electrical bone growth promotion implant taken along line 8 of FIG. 7 showing the thread portion being anchored to and passing through a non-conductive material.
FIG. 9 is a side elevational view of a fourth alternative embodiment of the electrical bone growth promotion implant of the present invention having an external wire coil interposed between the external threads of the implant and insulated from the remainder of the implant by an non-electrically conductive insulating material.

Referring to FIGS. 7, 8A and 8B, a second alternative embodiment of the EBGP implant of the present invention is shown and generally referred to by the numeral 210. The EBGP implant 210 comprises a housing 230 similar to the housing 30 described above. The exterior of the housing 230 has external threads 200 which are formed on the outer circumference of the housing 230 preferably in a helix.

As shown in FIG. 8A, the threads 200 of the housing 230 are electrically conductive and have a non-conductive insulating material 202 separating the threads 200. The insulating material 202 may be ceramic or polyethylene or any other biocompatible material that has electrical insulating properties. In this second alternative embodiment, the housing 230 may be completely or partially hollow and threads 200 serve as the active cathode to conduct negative charge to the bone area in which the housing 230 is implanted and any material that may be within the housing 230. As the insulating material 202 is interposed between the threads 200 themselves and between the housing 230 itself, the threads 200 are isolated from the remainder of the housing 230 and essentially act as a coil that surrounds the exterior of the housing 230. The threads 200 are electrically connected to the cathode lead 74 (see FIG. 1) of the control circuitry 70 described above and thus the threads 200 function as a cathode to deliver negative charge from the EBGP implant 210 to the vertebrae V adjacent to the housing 230 and material contained within the housing 230 if any. The advantage of this arrangement is that only the coil threads 200 are charged rather than the external housing 230 and since the beneficial electrical effect to some instance from each of the threads 200, the threads 200 are an effective cathode lead with less current drain than would be required to charge the external housing 230.

As shown in FIG. 8B, it is possible to configure the threads 200 such that at least a portion thereof passes through the insulating material 202 and communicates with the central chamber 236 so as to also conduct electric charge to any material contained within the housing 230 as illustrated by the electrical field arrows. This design requires that either the inward or outward portions of the threads 200 not be continuous such that the integrity of the housing 230 is not substantially reduced. The housing 230 has macro-size openings 242 to permit bone-growth therethrough.

Figure 10:
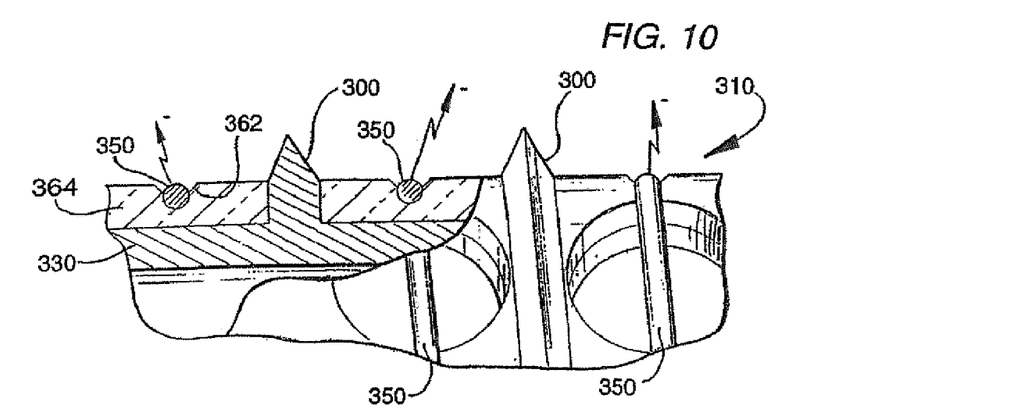
FIG. 10 is an enlarged fragmentary view taken along line 10 of FIG. 9 showing the external wire coil being held in place between the external threads of the implant by a non-electrically conductive insulating material.

Referring to FIGS. 9 and 10, a third alternative embodiment of the EBGP implant 310 of the present invention is shown and is generally referred to by the numeral 310. In the third embodiment, the EBGP implant 310 comprises a housing 330 similar to the housing 30 described above, having threads 300 and a wire 350 placed between the threads 300. The wire 350 is supported by a non conductive insulating material 364 that is placed between the threads 300 of the housing 330. The insulating material 364 has a groove 362 for receiving and holding the wire 350. The wire 350 is electrically coupled to a cathode lead such as the cathode lead 72 of the generator 60 (shown in FIG. 1) and is negatively charged such that wire 350 conducts bone growth promoting negative charge to the bone area of the adjacent vertebrae $V_1$ and $V_2$ adjacent to the coiled wire 350 and through the openings 342 to the fusion mass within the housing 330. The insulating material 364 prevents the body of the housing 330 from becoming electrically charged and prevents electrical conduction between wire 350 and threads 300 and housing 330 and any short circuiting of the coiled wire 350. In this manner, the area of the EBGP implant 310 which is electively charged is limited to the coiled wire 350 to significantly reduce the total area which is electrically charged. However, as the coiled wire 350 essentially extends approximately the entire longitudinal length of the EBGP 310, it is possible to deliver electrical charge to the entire area of bone adjacent to the EBGP 310 to stimulate bone growth without any diminished effect. Thus, the EBGP implant 310 is energy efficient since the amount of electrical current required to power the EBGP implant 310 is substantially less than that required for an implant where the entire implant housing is charged.

Referring to FIGS. 11-15, a fourth alternative embodiment of the EBGP implant 410 of the present invention is shown and is generally referred to by the numeral 410. In the fourth embodiment, the EBGP implant 410 comprises a housing 430 similar to the housing 30 and having an opening 420 having an axis that is perpendicular to the longitudinal axis L of the housing 430. The opening 420 passes through the housing 430 and communicates with the central chamber 436 of the housing 430 and is surrounded by four structural support members 421, 422, 423, and 424. The opening 420 is covered by a lattice 415 at both ends. The lattice 415 has openings 416 sufficiently sized to permit bone growth therethrough yet remains capable of retaining any natural or artificial bone growth material that may be contained within the hollow central chamber 436.

Figure 15:
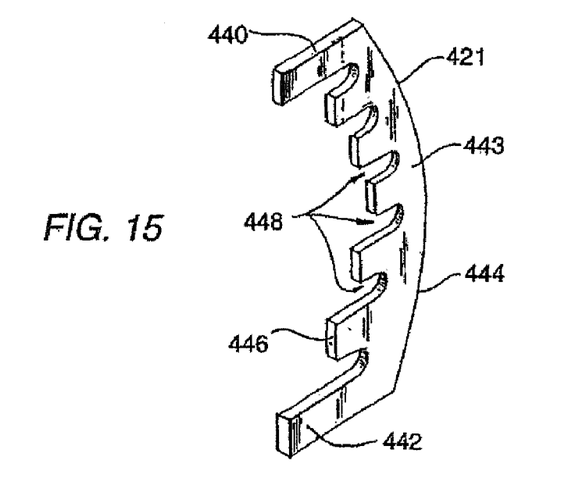
FIG. 15 is a perspective view of a structural support member used to support a wire coil coaxial with the vertical opening of the electric bone growth promotion implant of the present invention.

Referring to FIG. 15, an enlarged perspective view of structural support member 421 is shown. Each of the structural support members 421, 422, 423, and 424 are identical such that the description of one applies to each of the others. The structural support member 421 made of an electrically non-conductive material, has an upper arm 440 and a lower arm 442 that are placed in the hollow central chamber 436 and are secured to the spinal implant 410; a central portion 443 having a curved outer edge 444; and a grooved inner edge 446. The inner edge 446 of the structural support member 421 has a plurality of grooves 448 for receiving and holding a wire 425 capable of conducting electrical current. The plurality of grooves 448 are offset from each other and follow the curvature of the outer edge 444 of the structural support member 421.

Referring back to FIG. 11, preferably the four structural support members 421-424 are arranged around the outer perimeter of the opening 420 such that they are equidistant from one another. The wire 425 is placed within the grooves 448 and coiled about the four structural support members 421-424 to form a wire coil 426 around the perimeter of the opening 420 substantially along the entire vertical length of the opening 420 that is coaxial with the opening 420.

Figure 11:
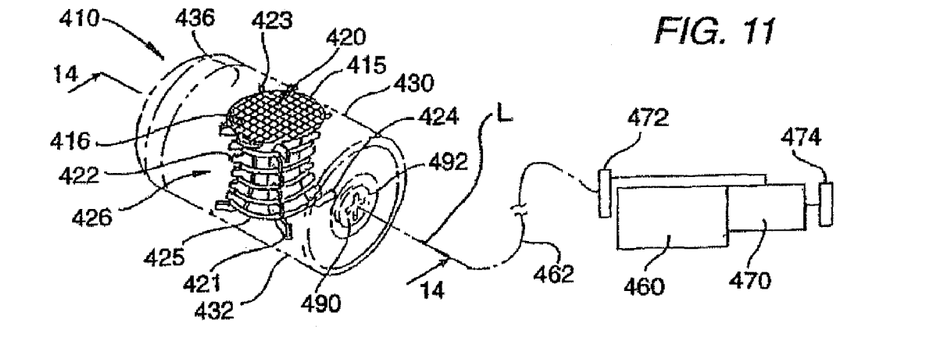
FIG. 11 is a perspective view of a fifth alternative embodiment of the electrical bone growth promotion implant of the present invention having an opening surrounded by a wire coil coaxial with the opening electrically connected to a remote power source.

The wire coil 426 is electrically coupled to a cathode lead 472 and delivers and delivers a negative charge to the area surrounding within the torroid opening 420 such that bone growth is promoted and stimulated by the presence of negative charge along the inner and outer walls of the torroid shaped wire coil 426. When the EBGP implant 410 is implanted between two adjacent vertebrae $V_1$ and $V_2$, the opening 420 is filled with bone or bone promotion substances and the electrical promotion of bone growth causes bone of the adjacent vertebrae $V_1$ and $V_2$ to grow into and through the vertical opening 420 into that bone or bone promoting substances from one vertebra $V_1$ to the other vertebrae $V_2$.

Figure 12:
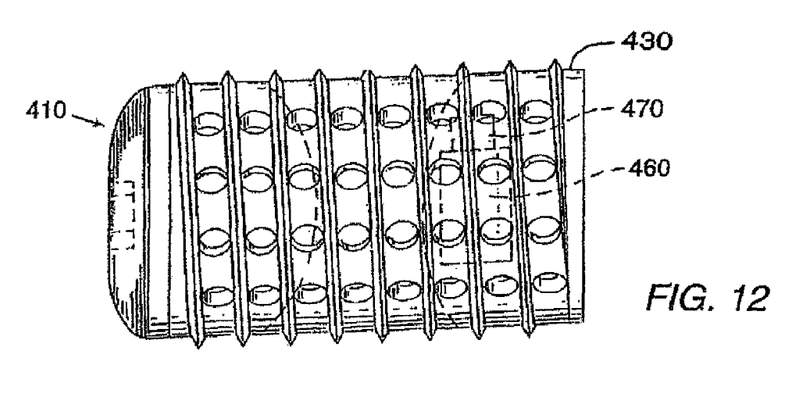
FIG. 12 is a side view of a sixth alternative embodiment of the electrical bone growth promotion implant of the present invention having an opening surrounded by a wire coil coaxial with the opening and electrically coupled to an internal power source.
Figure 13:
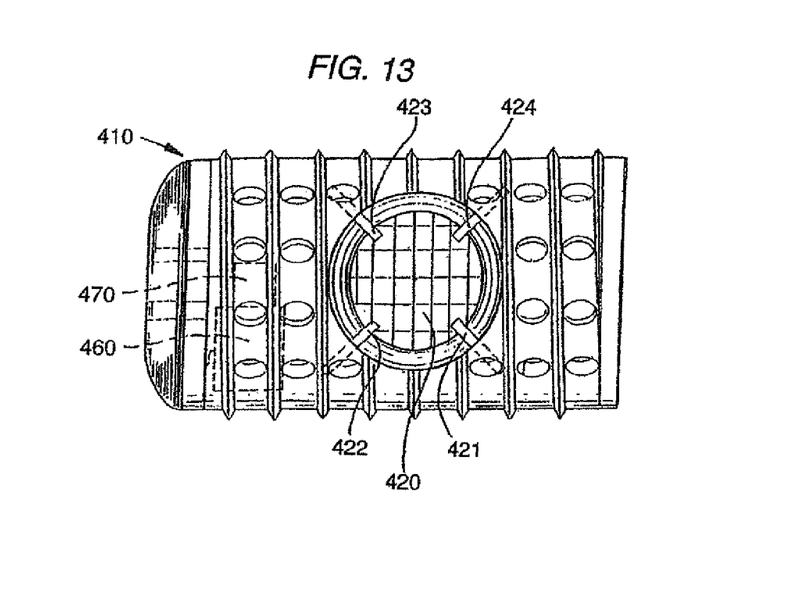
FIG. 13 is a top plan view of the electrical bone growth promotion implant of FIG. 12 showing the opening.

As shown in FIGS. 12 and 13, the control circuitry 470 and the power supply 460 are contained within the central chamber 436 of the housing 430 such that the EBGP implant 410 is a self-contained unit. The wire coil 426 is coupled directly to a cathode lead 472 such that the wire coil 426 becomes negatively charged.

Figure 14:
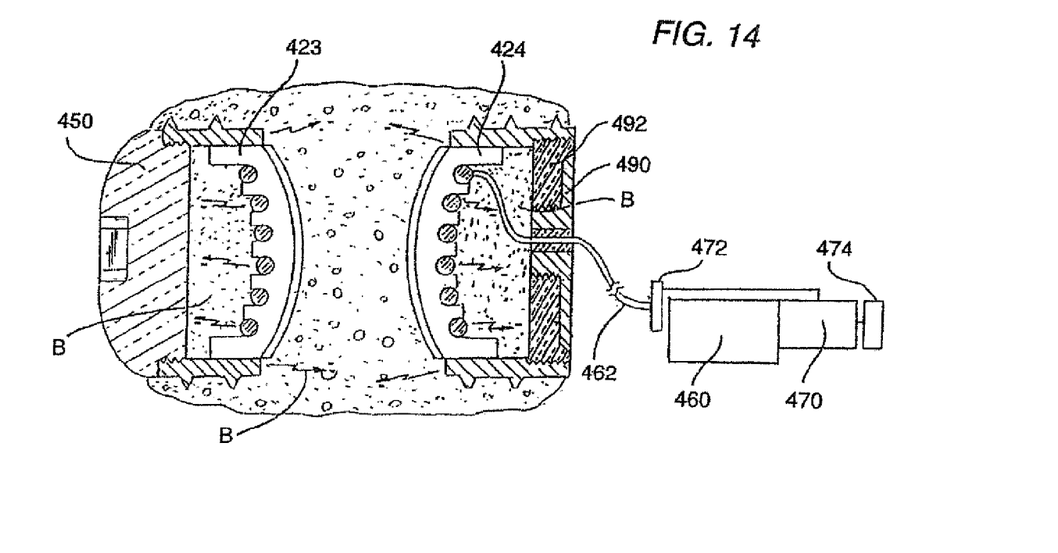
FIG. 14 is a cross sectional side elevation view along lines 14-14 of FIG. 11 of the bone growth promotion implant of the present invention having an external power source and illustrating the bone growth from one vertebra to a second adjacent vertebra that occurs during the spinal fusion process.

As shown in FIGS. 11 and 14, alternatively, the control circuitry 470 and power supply 460 may be implanted in an area of the patient's body remote from the EBGP implant 410. The cathode lead 472 may be coupled directly to the wire coil 426 via lead wire 462 or may be coupled to the body of the housing 430 which is electrically conductive, and the wire coil 426 may also be electrically coupled to the housing 430 so that the housing 430 becomes electrically charged. However, it is preferred that the wire coil 426 be connected to either a wire coil such as described above in reference to FIGS. 9 and 10 or threads 200 as described above in reference to FIGS. 7, 8A and 8B. In this manner, efficient use of the power supply 460 is made as the drain is reduced without diminishing the effectiveness of the electrical promotion of bone growth as discussed above.

Figures 16, 17, 18, 19:
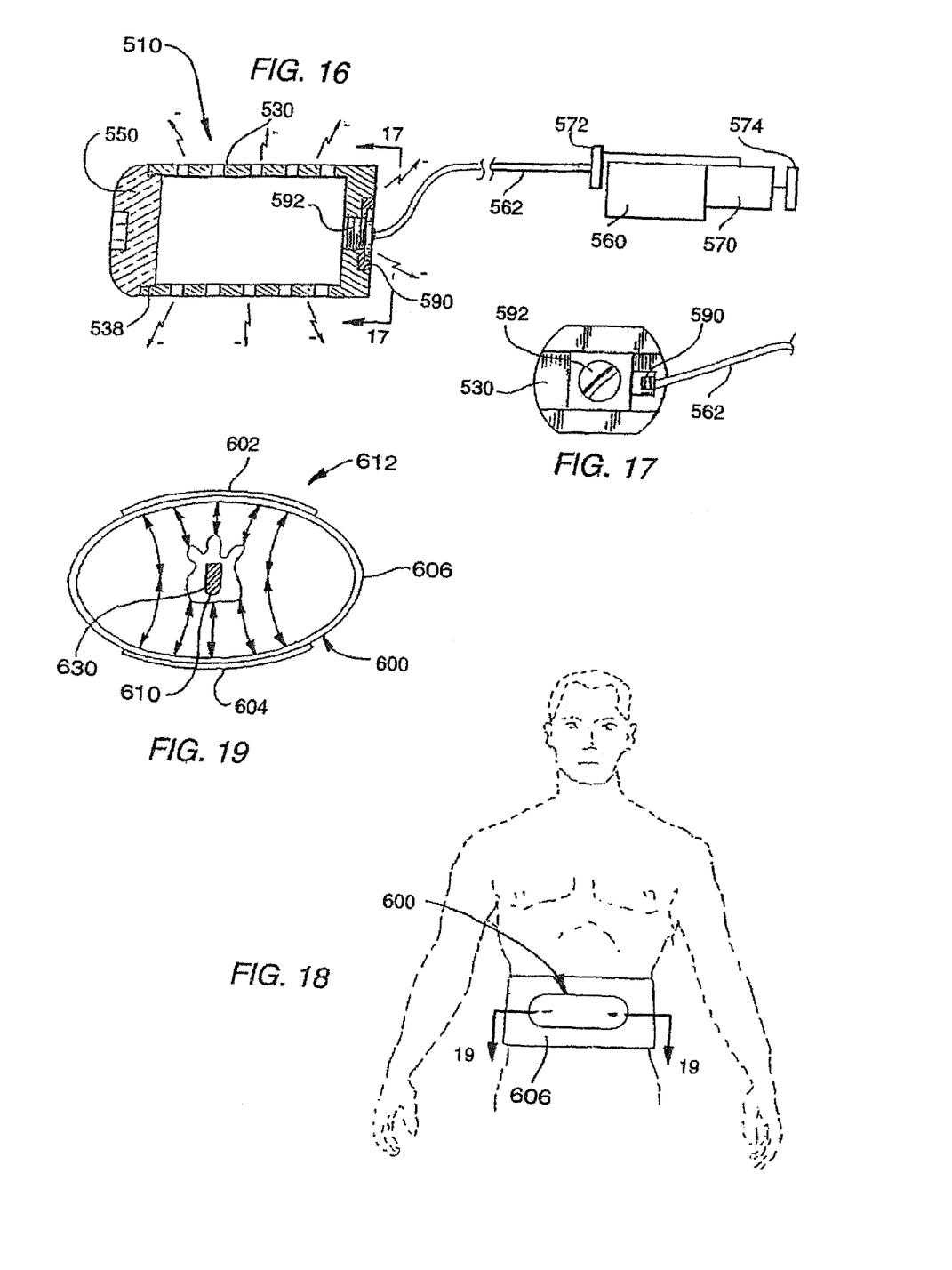

Referring to FIGS. 16 and 17 a fifth alternative embodiment of the EBGP implant 510 of the present invention is shown. The EBGP implant 510 comprises a housing 530 having a non-electrically conductive cap 550 threaded to its distal end 538, and a remotely implanted power supply 560 and control circuitry 570 connected to the housing 530. As the cap 550 is non-conductive, the housing 530 itself is negatively charged when coupled to the cathode lead 572 and the cap 550 has no electrical charge. The power supply 560 is electrically connected to the housing 530 by the lead wire 562 which terminates at a connector 590 which is attached by a screw 592 to the housing 530.

It is appreciated that a remotely implanted power supply and/or related control circuitry may be used to deliver electric current to any of the embodiments described above that are self-contained units having an internal power supply and generator, without departing from the scope of the present invention.

Referring to FIGS. 18 and 19 a sixth alternative embodiment of the EBGP system 612 of the present invention is shown. In the sixth alternative embodiment, the EBGP implant 610 comprises an electromagnetic field transmitter 600 that is worn external to the patient's body. The transmitter 600 has two portions 602 and 604 which are secured to the patient's body by a band 606 or any other suitable means, such that each portion 602, 604 is placed on opposite sides of the body at the exterior of the patient's body.

Implanted between two adjacent vertebrae $V_1$ and $V_2$ of the patient is a housing 630 similar to the housing 30 described above. The housing 630 is at least in part ferromagnetic and thereby capable of being inductively coupled to the electromagnetic fields transmitted by the transmitter 600. The EBGP implant 610 thereby may be inductively coupled to transmitter 600 and in this manner electromagnetic fields and resultant induced electrical currents in EBGP implant 610 may be concentrated and directed to a location in which bone growth is desired without the need for surgically implanting a power supply and/or control circuitry within the housing 630 or within the body of the patient. The non-ferromagnetic portion of the housing 630 also may be electrically conductive, which would make the housing 630 capable of being inductively coupled to the electromagnetic fields transmitted by the transmitter 600 as well as a conductor of electrical currents induced by said externally applied electromagnetic fields.

Similarly, if a rechargeable power supply 460 (FIG. 12) is contained within the housing 630, the power supply may be recharged with the application of external electromagnetic fields via the transmitter 600. Thus, the power supply in implant 610 could be much smaller in size as the power supply may be repeatedly recharged. In this manner, both the housing 630 and the power supply therein may be inductively coupled to the transmitter 600, such that the housing 630 delivers electrical current to the adjacent bone mass and the power supply is being recharged. After the transmitter 600 is no longer inductively coupled to the EBGP implant 610 the replenished power supply in implant 610 continues to deliver electrical current to the housing 630. In this manner, the period of time in which a patient must wear the transmitter is substantially reduced to the period of time required to replenish the power supply, while maintaining a continuous delivery of electrical current to the housing 630.

As a further alternative, a rechargeable power supply may be implanted remote to the spine, preferably subcutaneously, such that the power supply is easily rechargeable via electromagnetic induction. The inductive coupling of a subcutaneous power supply with the electromagnetic transmitter 600 overcomes the problems of infection associated with any direct coupling of a power supply to a power source. Further, subcutaneous implantation of the power supply also facilitates explantation of the power supply and further reduces the risk of infection to the patient. In contrast to implantations in other areas of the body.

Figure 20:
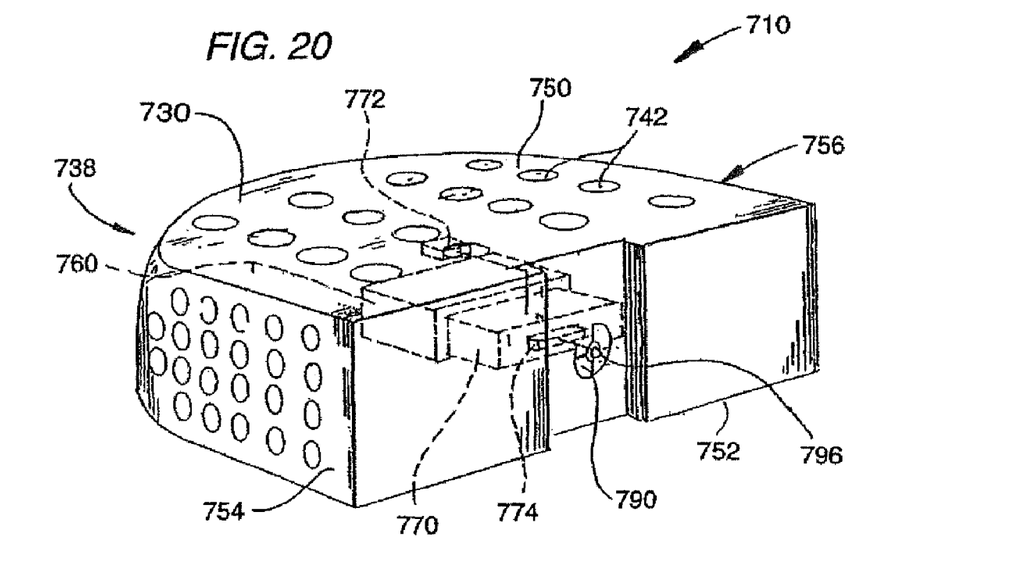
FIG. 20 is a perspective side view of an eighth alternative embodiment of the electric bone growth promotion implant of the present invention having an internal power supply and generator shown in hidden line.

Referring to FIG. 20 a seventh alternative embodiment of the EBGP implant 710 of the present invention is shown. In the seventh embodiment, the housing 730 has a substantially rectangular hollow configuration and has a tapered distal end 738. The housing 730 has an upper surface 750 and a parallel lower surface 752 and two side walls 754 and 756. The housing 730 has a series of small openings 742 through the upper and lower surfaces 750 and 752 and through the side walls 754 and 756 for permitting bone growth there through. Contained within the spinal implant 710 are the power supply 760 and the control circuitry 770 so that the spinal implant 730 is a self-contained unit. The power supply 760 and/or control circuitry 770 are electrically coupled to the housing 730 by a cathode lead 772 and an anode lead 774. The anode lead 774 is coupled to an insulating screw 790 having an electrically conductive core 796. The insulating screw 790 is threaded into the EBGP implant 710 and insulates the anode lead 774 from the rest of the EBGP implant 710.

Figure 21:
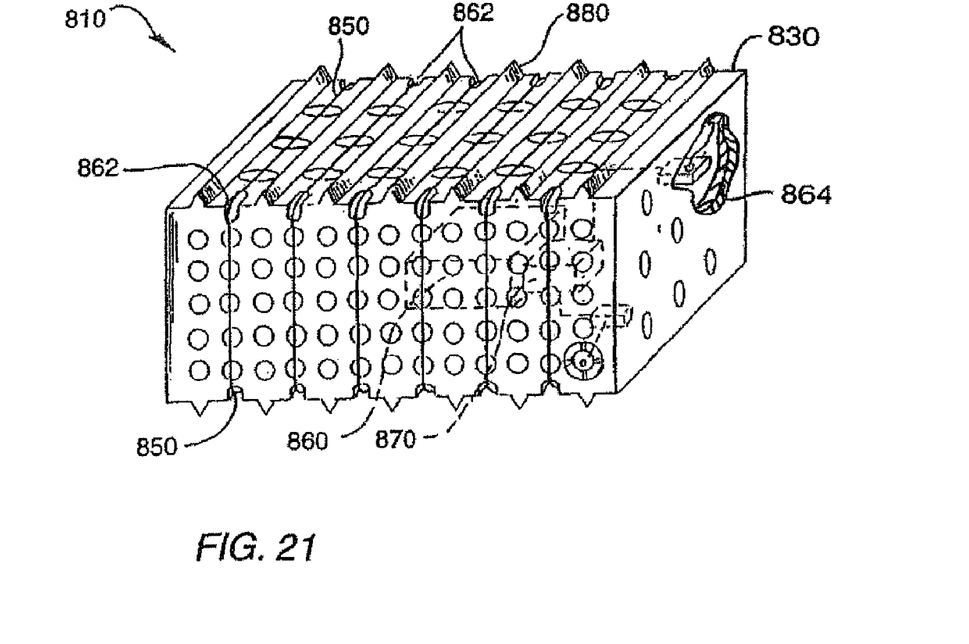
FIG. 21 is a perspective view of a ninth alternative embodiment of the electric bone growth promotion implant of the present invention having an internal power supply and generator shown in hidden line.

Referring to FIG. 21 an eighth alternative embodiment of the EBGP implant 810 of the present invention is shown. The EBGP implant 810 is much like the seventh alternative embodiment except that the housing 830 has a hollow rectangular configuration with raised engagement teeth 880 for engaging the bone of adjacent vertebra V and has a wire 850 similar to wire 350 described above, coiled about the housing 830. The wire 850 is insulated from the housing 830 by an insulating material 864 having a groove 862 for receiving the wire 850. The insulating material 864 is identical to insulating material 364 discussed above. The EBGP implant 810 is also a self-contained unit as the power supply 860 and/or control circuitry 870 are contained within the hollow chamber of the spinal implant 810 and are electrically coupled to the wire 850.

It is appreciated that the EBGP implant of the present invention is not limited to use in the spinal fusion process but is also applicable to promoting almost any fusion of a large joint and for promoting healing of a fracture of any of the major bones of the body. Furthermore, the apparatus and method of the present invention may be incorporated into various total knee arthroplasty and total hip arthroplasty. Such implants may embody the above-described teachings without departing from the scope of the present invention. Such implants may be wholly or partially electrically conductive having a permanent or rechargeable power supply and related control circuitry located within the implant itself such that the implant is a self-contained unit. The use of a renewable power source is of great advantage with such implants in that the bone fusion process, or the healing of the larger bones such as the femur or hip, for example, may require a longer period of time for bone healing fusion than the service life of the implantable permanent power supplies that are presently utilized. As discussed above in greater detail, the recharging of the power source through external charging can extend the delivery of electrical current to the site in which induction of osteogenesis is desired for a substantially greater period of time.

Further, such implants may also comprise externally applied electromagnetic coils to generate an electromagnetic field that may be inductively coupled to the implant which in turn delivers electrical charges to the areas of bone adjacent to the implant as described in greater detail above and recharge the power supply by electromagnetic induction from an externally applied electrical field. All of such implants have the added advantage in that once implanted they become permanently entombed within the bone fusion mass after completion of the fusion process and need not be surgically removed.

While the present invention has been described in detail with regards to the preferred embodiments, it is appreciated that other variations of the present invention may be devised which do not depart from the inventive concept of the present invention.

What is claimed is:

1. An artificial spinal implant for insertion into an implantation space created between two adjacent vertebral bone masses, comprising:
   a housing including:
   an upper surface and a lower surface opposite said upper surface, said upper and lower surfaces being configured to contact and support the adjacent vertebral bone masses;
   a leading end for insertion first into the implantation space and a trailing end opposite said leading end;
   opposite sides from said upper surface to said lower surface, and from said leading end to said trailing end;
   a mid-longitudinal axis passing through said leading and trailing ends;
   a maximum width from one of said opposite sides to the other of said opposite sides;
   a height from said lower surface to said upper surface;
   a depth from said leading end to said trailing end, the maximum width of said housing being greater than each of the height and depth of said housing, said leading end being curved from said opposite side to said opposite side; and
   a hollow chamber;
   control circuitry in said hollow chamber; and
   a rechargeable power supply for energizing said control circuitry, said rechargeable power supply being configured for inductive coupling to an external power supply.

2. The implant of claim 1, wherein said upper and lower surfaces are configured for bone ingrowth.

3. The implant of claim 1, wherein said upper and lower surfaces include surface roughenings.

4. The implant of claim 1, further comprising an opening having a central longitudinal axis perpendicular to the mid-longitudinal axis of said housing.

5. The implant of claim 4, wherein said opening having the central longitudinal axis that is perpendicular to the mid-longitudinal axis of said housing as an inner perimeter different to an inner perimeter of said closeable opening.

6. The implant of claim 5, wherein the inner perimeter of said closeable opening is larger than the inner perimeter of said opening having the central longitudinal axis that is perpendicular to the mid-longitudinal axis of said housing.

7. The implant of claim 1, wherein said control circuitry is hermetically sealed within said housing.

8. The implant of claim 1, wherein said rechargeable power supply is a rechargeable battery.

9. The implant of claim 1, further comprising an external power supply for inductively recharging said rechargeable power supply.

10. The implant of claim 9, wherein said external power supply includes a belt with an electromagnetic transmitter.

11. The implant of claim 9, wherein said external power supply includes an electromagnetic belt coil.

12. The implant of claim 1, wherein said housing includes a portion made of titanium.

13. The implant of claim 1, wherein said implant is a spinal fusion implant.

14. The implant of claim 1, wherein said upper and lower surfaces include a plurality of openings adapted to allow bone growth from each of the adjacent vertebral bodies through said hollow chamber.

15. The implant of claim 1, wherein said trailing end includes a vertical indented portion along the height of said housing, said vertical indented portion being centered along approximately one-half of the maximum width of said housing.

16. The implant of claim 1, wherein said housing includes an opening to said hollow chamber, said opening being closeable.

17. An artificial spinal implant for insertion into an implantation space created between two adjacent vertebral bone masses, comprising:
a housing including:
an upper surface and a lower surface opposite said upper surface, said upper and lower surfaces being configured to contact and support the adjacent vertebral bone masses, said upper and lower surfaces including a plurality of engagement teeth;
a leading end for insertion first into the implantation space and a trailing end opposite said leading end;
opposite sides from said upper surface to said lower surface, and from said leading end to said trailing end;
a mid-longitudinal axis passing through said leading and trailing ends;
a maximum width from one of said opposite sides to the other of said opposite sides;
a height from said lower surface to said upper surface, the maximum width of said housing being greater than the height of said housing; and
a hollow chamber;
control circuitry in said hollow chamber;
a rechargeable power supply for energizing said control circuitry, said rechargeable power supply being configured for inductive coupling to an external power supply; and
an induction coil, a portion of said housing being made from a metallic material, said housing including an insulating material insulating said induction coil from said metallic portion of said housing.

18. The implant of claim 17, wherein said upper and lower surfaces are configured for bone ingrowth.

19. The implant of claim 17, further comprising an opening having a central longitudinal axis perpendicular to the mid-longitudinal axis of said housing.

20. The implant of claim 19, wherein said opening having the central longitudinal axis that is perpendicular to the mid-longitudinal axis of said housing as an inner perimeter different to an inner perimeter of said closeable opening.

21. The implant of claim 20, wherein the inner perimeter of said closeable opening is larger than the inner perimeter of said opening having the central longitudinal axis that is perpendicular to the mid-longitudinal axis of said housing.

22. The implant of claim 19, wherein each of said engagement teeth has a forward facing facet and a reward facing facet inclined towards each other to form a peak, the peak of each of said engagement teeth forming a linear portion parallel to the central longitudinal axis of said opening having the central longitudinal axis that is perpendicular to the mid-longitudinal axis of said housing.

23. The implant of claim 17, wherein said control circuitry is hermetically sealed within said housing.

24. The implant of claim 17, wherein said rechargeable power supply is a rechargeable battery.

25. The implant of claim 17, further comprising an external power supply for inductively recharging said rechargeable power supply.

26. The implant of claim 25, wherein said external power supply includes a belt with an electromagnetic transmitter.

27. The implant of claim 25, wherein said external power supply includes an electromagnetic belt coil.

28. The implant of claim 17, wherein said metallic material is titanium.

29. The implant of claim 17, wherein said implant is a spinal fusion implant.

30. The implant of claim 17, wherein said upper and lower surfaces include a plurality of openings adapted to allow bone growth from each of the adjacent vertebral bodies through said hollow chamber.

31. The implant of claim 17, wherein said induction coil is wound along an exterior surface of said housing.

32. The implant of claim 17, wherein said engagement teeth are spaced apart from one another.

33. The implant of claim 17, wherein said engagement teeth extend along the entire width of said housing.

34. The implant of claim 17, wherein said housing includes an opening to said hollow chamber, said opening being closeable.

* * * * *